(12) United States Patent
Gagliardoni et al.

(10) Patent No.: US 10,286,203 B2
(45) Date of Patent: *May 14, 2019

(54) NEEDLEFREE VALVE DEVICE

(71) Applicant: Cedic s.r.l., Peschiera Borromeo (MI) (IT)

(72) Inventors: Giancarlo Gagliardoni, Estado Miranda (VE); Jan Willem Marinus Mijers, Haarlem (NL)

(73) Assignee: Cedic S.R. L., Peschiera Borromeo (IT)

( * ) Notice: Subject to any disclaimer, the term of this patent is extended or adjusted under 35 U.S.C. 154(b) by 26 days.

This patent is subject to a terminal disclaimer.

(21) Appl. No.: 14/912,202

(22) PCT Filed: Aug. 21, 2013

(86) PCT No.: PCT/EP2013/067361
§ 371 (c)(1),
(2) Date: Feb. 16, 2016

(87) PCT Pub. No.: WO2015/024594
PCT Pub. Date: Feb. 26, 2015

(65) Prior Publication Data
US 2016/0199634 A1  Jul. 14, 2016

(51) Int. Cl.
*A61M 39/26* (2006.01)
*A61M 39/04* (2006.01)
(Continued)

(52) U.S. Cl.
CPC ........ *A61M 39/26* (2013.01); *A61M 39/1011* (2013.01); *A61M 39/22* (2013.01);
(Continued)

(58) Field of Classification Search
CPC .................. A61M 39/22; A61M 39/26; A61M 2039/267; A61M 2039/268;
(Continued)

(56) References Cited

U.S. PATENT DOCUMENTS 2,073,048 A * 3/1937 Clark ...................... F16K 31/58
251/149.5
3,140,072 A * 7/1964 Scinto, Jr. ............... F16L 37/23
251/100
(Continued)

FOREIGN PATENT DOCUMENTS

| WO | 2006/062912 | 6/2006 |
| WO | 2010/111546 | 9/2010 |
| WO | 2012/151222 | 11/2012 |

OTHER PUBLICATIONS

International Preliminary Report on Patentability and Written Opinion for International Application No. PCT/EP2013/067361.

*Primary Examiner* — Reinaldo Sanchez-Medina
*Assistant Examiner* — David Colon-Morales
(74) *Attorney, Agent, or Firm* — Jansson Munger McKinley & Kirby Ltd.

(57) ABSTRACT

Needle free valve device (1) for controlling the flow of fluid in a pathway, the device (1) being operable in a closed and in an open configuration and comprising a first component (3), a second component (9), a locking means configured to selectively engage the first component (3) with the second component (9) in the open configuration when the first component (3) is displaced in an opening direction (23) along a valve axis toward the second component (9) or in the closed configuration when the first component (3) is displaced against the opening direction (23) away from the second component (9), and a sealing component (15) having a resilient portion (19), the resilient portion (19) comprising at least one slit (26) and engaging the second component (9) to provide a seal in the closed configuration, wherein the resilient portion (19) is adapted to move, buckle or flex to enable fluid flow through the at least one slit (26) upon application of a mechanical force of the second component (9) on the resilient portion (19) against the opening direction (Continued)

(23) when assuming the open configuration, and wherein the resilient portion (19) is adapted to return the valve device (1) to the closed configuration when the mechanical force is no longer applied.

11 Claims, 9 Drawing Sheets

(51) Int. Cl.
*A61M 39/10* (2006.01)
*A61M 39/22* (2006.01)

(52) U.S. Cl.
CPC ... *A61M 39/045* (2013.01); *A61M 2039/1083* (2013.01); *A61M 2039/1088* (2013.01); *A61M 2039/267* (2013.01)

(58) Field of Classification Search
CPC .. A61M 2039/1083; A61M 2039/1088; A61M 39/045; A61M 39/10; A61M 39/1011; A61M 2039/1016; A61M 2039/1044; A61M 39/06; A61M 39/24; F16L 29/02; F16L 29/04; F16L 37/48; F16L 37/40; F16L 37/413; F16L 37/42; F16L 37/0985; F16L 37/107; F16L 37/113; F16L 37/133; F16L 37/24; F16L 37/248; Y10T 137/87933; Y10T 137/87941; Y10T 137/87949; Y10T 137/87957; Y10T 137/87965; A61J 1/1481
USPC ......... 251/149.1, 149.4, 149.5, 149.6, 149.8, 251/149.9, 215, 251–261, 351, 346, 296, 251/89.5, 107–109, 111, 113, 115; 285/314, 376, 377, 401, 402, 317, 319, 285/331, 361, 396
See application file for complete search history.

(56) References Cited

U.S. PATENT DOCUMENTS

| | | | | | |
|---|---|---|---|---|---|
| 3,620,500 | A | * | 11/1971 | Santomieri | A61M 5/16877 138/45 |
| 3,955,647 | A | * | 5/1976 | Tine | F01M 1/08 184/39.1 |
| 4,306,743 | A | * | 12/1981 | Hinshaw | F16L 37/248 285/260 |
| 4,610,469 | A | * | 9/1986 | Wolff-Mooij | A61M 39/045 251/149.1 |
| 4,982,736 | A | * | 1/1991 | Schneider | A61F 7/02 137/614.04 |
| 5,096,158 | A | * | 3/1992 | Burdick | F01M 11/0408 137/315.25 |
| 5,228,646 | A | * | 7/1993 | Raines | A61M 39/22 251/322 |
| 5,269,771 | A | * | 12/1993 | Thomas | A61M 39/045 251/149.1 |
| 5,549,577 | A | * | 8/1996 | Siegel | A61M 39/045 251/149.1 |
| 5,738,663 | A | * | 4/1998 | Lopez | A61M 39/10 604/249 |
| 5,762,646 | A | * | 6/1998 | Cotter | A61J 1/1412 285/303 |
| 5,788,215 | A | * | 8/1998 | Ryan | A61J 1/2096 251/149.6 |
| 5,806,831 | A | * | 9/1998 | Paradis | A61M 39/02 251/149.1 |
| 5,839,715 | A | * | 11/1998 | Leinsing | A61J 1/2096 251/149.1 |
| 5,871,471 | A | * | 2/1999 | Ryan | A61B 17/3496 137/849 |
| 5,901,942 | A | * | 5/1999 | Lopez | A61M 5/14 251/149.1 |
| 5,960,819 | A | * | 10/1999 | Weissinger | B60K 15/03519 137/315.11 |
| 6,029,946 | A | * | 2/2000 | Doyle | A61M 39/26 251/149.1 |
| 6,050,978 | A | * | 4/2000 | Orr | A61M 39/26 251/149.1 |
| 6,113,068 | A | * | 9/2000 | Ryan | A61M 39/045 251/149.4 |
| 6,196,522 | B1 | * | 3/2001 | Yuen | B67D 7/0288 222/501 |
| 6,651,956 | B2 | | 11/2003 | Miller | |
| 6,755,391 | B2 | * | 6/2004 | Newton | A61M 39/26 251/149.1 |
| 6,866,243 | B2 | * | 3/2005 | Yang | F16L 37/252 251/149.5 |
| 6,994,315 | B2 | * | 2/2006 | Ryan | A61M 39/26 251/149.3 |
| 7,040,598 | B2 | * | 5/2006 | Raybuck | A61M 39/26 251/149.1 |
| 7,044,441 | B2 | * | 5/2006 | Doyle | A61M 39/045 251/149.3 |
| 7,118,560 | B2 | * | 10/2006 | Bonaldo | A61M 39/26 604/248 |
| 7,350,535 | B2 | * | 4/2008 | Liepold | A61M 39/10 137/553 |
| 7,470,262 | B2 | * | 12/2008 | Hiejima | A61M 39/26 604/167.04 |
| 7,490,620 | B2 | * | 2/2009 | Tesluk | A61M 39/105 137/15.09 |
| 7,530,546 | B2 | * | 5/2009 | Ryan | A61M 39/26 251/149.6 |
| 7,559,530 | B2 | * | 7/2009 | Korogi | A61B 5/15003 251/149.6 |
| 7,631,660 | B2 | * | 12/2009 | deCler | A61M 39/18 137/614.03 |
| 7,824,393 | B2 | * | 11/2010 | Fangrow | A61M 39/26 604/256 |
| 7,918,243 | B2 | * | 4/2011 | Diodati | A61M 39/18 137/614.03 |
| 8,025,646 | B2 | * | 9/2011 | Fukai | A61M 39/045 604/256 |
| 8,092,409 | B2 | * | 1/2012 | Mros | A61M 39/12 285/124.2 |
| 8,105,314 | B2 | * | 1/2012 | Fangrow, Jr. | A61M 39/10 251/149.1 |
| 8,133,209 | B2 | * | 3/2012 | Guala | A61M 39/045 604/167.03 |
| 8,205,917 | B2 | * | 6/2012 | Brewer | A61M 16/0816 285/361 |
| 8,377,039 | B2 | * | 2/2013 | Utterberg | A61M 39/02 604/533 |
| 8,454,579 | B2 | * | 6/2013 | Fangrow, Jr. | A61M 39/24 604/539 |
| 2003/0098430 | A1 | | 5/2003 | Leinsing | |
| 2006/0189961 | A1 | * | 8/2006 | Miyahara | A61M 39/14 604/535 |
| 2008/0197626 | A1 | * | 8/2008 | Coambs | A61M 39/26 285/330 |
| 2009/0069783 | A1 | * | 3/2009 | Ellstrom | A61M 39/1011 604/415 |
| 2009/0177170 | A1 | * | 7/2009 | Kitani | A61M 39/26 604/256 |
| 2010/0211019 | A1 | * | 8/2010 | Greco | A61J 1/1437 604/246 |
| 2011/0015566 | A1 | * | 1/2011 | Pan | A61M 39/26 604/68 |
| 2011/0060312 | A1 | * | 3/2011 | Scheurer | A61M 5/14244 604/523 |
| 2011/0074148 | A1 | * | 3/2011 | Imai | A61J 1/2089 285/308 |
| 2011/0125128 | A1 | * | 5/2011 | Nord | A61J 1/2096 604/414 |
| 2012/0130305 | A1 | * | 5/2012 | Bonnal | A61M 39/02 604/30 |

(56) References Cited

U.S. PATENT DOCUMENTS

| | | | | |
|---|---|---|---|---|
| 2012/0157914 A1* | 6/2012 | Stroup | ............... | A61M 39/26 |
| | | | | 604/68 |
| 2012/0192968 A1* | 8/2012 | Bonnal | ............. | A61M 39/1011 |
| | | | | 137/454.2 |
| 2013/0270820 A1* | 10/2013 | Py | ..................... | F16L 37/24 |
| | | | | 285/330 |
| 2013/0292592 A1* | 11/2013 | Py | ..................... | F16L 29/02 |
| | | | | 251/149.6 |

* cited by examiner

NEEDLEFREE VALVE DEVICE

CROSS-REFERENCE TO RELATED APPLICATION

The present application is a U.S. national phase entry of pending International Patent Application No. PCT/EP2013/067361, international filing date Aug. 21, 2013, the contents of which are incorporated by reference in its entirety.

FIELD OF THE INVENTION

The present invention generally relates to valve devices of the type used in the handling and administration of fluids, and more particularly to a needlefree medical valve device adapted to be used in any type of tube connection such as between the different kinds of ports and syringes, catheters, pumps, or the like which are used in the administration of all kinds of fluids. Examples of such administration are intravenous, enteral or parenteral delivery of fluids to or from a body.

BACKGROUND OF THE INVENTION

Needlefree valve connectors are known in the art of reducing the accidental needle stick exposure to medical personnel, reducing the risk of contamination and patient infection due to repeat needle sticks to the ports, and providing easy connection and disconnection without compromising sterility.

EP 2 269 687 A2 discloses a connector for controlling the flow of fluid the construction of which is complex and comprises a number of limitations.

Some of the known needlefree medical connectors are repeatedly connectable with a range of other medical implements and are self-sealing when disconnected from other medical implements. Examples of such needlefree medical connectors are disclosed in WO 2010/111546 A2, WO 2006/062912 A1, and WO 2012/151222 A1 which is "configured to operate similar to the valve stem shown and described in U.S. Pat. No. 6,651,956" incorporated therein. The structures of these connectors are complex, thus leading to high manufacturing costs.

Different types of connectors are used throughout various kinds of medical fields such as intravenous administration, enteral or parenteral administration, for the taking of blood samples, for artificial ventilation or respiration and the like. These different types of connections must not be mixed up because lethal misconnections must be avoided. Therefore, there are standardized configurations which are intended to regulate the usage of different connectors with different sizes such that misconnections cannot occur.

It is therefore an object of the present invention to remedy or reduce at least one of the shortcomings of the prior art and to provide a needlefree valve device or connector having a relatively simple structure, which offers a wide variety of connection possibilities and is also self-sealing when disconnected from other ports.

SUMMARY OF THE INVENTION

According to an aspect of the invention, a needlefree valve device for controlling the flow of fluid in a pathway is provided, the connector being operable in a closed and in an open configuration and comprising a first component, a second component, a locking mechanism configured to selectively engage the first component with the second component in the open configuration when the first component is displaced in an opening direction along a valve axis toward the second component or in the closed configuration when the first component is displaced against the opening direction away from the second component, and a sealing component having a resilient portion, the resilient portion comprising at least one slit and engaging the second component to provide a seal in the closed configuration, wherein the resilient portion is adapted to move, buckle or flex to enable fluid flow through the at least one slit upon application of a mechanical force of the second component on the resilient portion against the opening direction when assuming the open configuration, and wherein the resilient portion is adapted to return the valve device to the closed configuration when the mechanical force is no longer applied.

The structure of the valve device (it can also be said to be a valve connector as in the previously mentioned prior art documents) is rather simple since it is comprised of only three main components which are produced using known technologies such as injection molding. Also, the setup, managing and handling of the valve device is free of complex procedural steps. In the closed position of the valve device, the second component and the resilient portion provide a sufficient sealing of the valve due to the slight pretension when the second component and the resilient portion are engaged with each other. This keeps the flexible and elastic material of the resilient portion compressed so that any fluid is prevented from flowing through the passageway. Further, the simple structure of the valve device offers various possibilities for the design of the connecting ports of the first and the second component. Thus, a large number of standardized or customized connector types including tube mating ports may be applied to either end of the valve device.

Preferably, the first component, the second component and the sealing component are substantially axially symmetric with respect to the valve axis and the locking mechanism is configured such that the first component is rotatable around the valve axis by a predetermined angle. As a large number of connector types, particularly in the medical field, have a circular cross-section and, for example, use threaded connecting portions or bayonet-type connections, the valve device of the present invention supports these kinds of connections where two components are connected by pressing the ports onto one another and subsequently turning the ports in a clockwise direction with respect to one another. Similar considerations apply for disconnecting two components in the counterclockwise direction. Thus, the valve device is highly compatible with practically any type of connector, particularly in the medical field.

It is preferred that the locking member (also referred to herein as a "locking mechanism") comprises a latch arranged on the second component adapted to engage with at least one corresponding recess in the first component (also referred to herein interchangeably as "locking-member engagers"). By this possibility to lock the valve device in the open or in the closed position, the safety of the valve device is highly increased. Particularly in the closed, locked position, the valve device can be disconnected from or connected to another component. The combination of a latch in engagement with a recess is only one possibility for the locking mechanism interlocking the first component with the second component. Other locking mechanisms such as a bayonet-type coupling may also be used.

It is especially preferred that the recess comprises a rectangular shape and a locking arm extending in a circumferential direction such that the latch of the second component is adapted to engage with the locking arm in the open and in the closed configuration. This structure of the locking mechanism takes into account that many connector types use threaded portions on at least one port. In a case where the first component includes a male Luer lock port, the corresponding female Luer component is screwed onto said male Luer lock port in a clockwise direction. When the user continues to connect the first component, now connected to the female Luer component, to the second component, the clockwise movement is generally continued such that the latch of the second component engages with the portion of the recess which is in the opening direction of the valve device, i.e. below the locking arm when the second component is generally located below the first component, until the stop is reached. In this position, the valve device is in the closed configuration, and it is a relatively stable configuration due to the fact that any force of opening the valve device must first counter the force inherent to the resilient portion. From this closed configuration the user can exert an (axial) force onto the first component to close the valve. Thus, a "self-opening" movement of the valve device without the use of a dedicated axial force is not possible. Such a dedicated axial opening force will disengage the latch from the lower recess portion and bring it in engagement with the upper recess portion, i.e. with the portion of the recess above the locking arm when the second component is generally located below the first component. It must be noted that the full functionality of the locking mechanism will be explained in detail with respect to the drawings below.

In a further preferred embodiment, the locking arm includes a spring element at its free end functioning as a stop for the latch in an axial direction. This will hold the latch in the lower portion of the recess, i.e. the closed configuration, in the case where the first component is rotated counter-clockwise with respect to the second component, because the spring element works as stop for the latch. However, in the case where the valve device is in the open configuration, the inherent restoring forces of the resilient portion will cause the valve device to assume the closed position because the spring element will give in due to its elasticity to the inherent closing force. In other words, the spring element of the locking arm works as stop against inadvertent opening or self-opening forces but will yield when the self-closing forces are applied. This feature therefore supports the self-sealing function of the valve device when counterclockwise rotation on the first component is performed for disconnection.

As an additional or alternative feature to the spring element feature of the locking arm the sealing component further comprises at least one resilient retention element arranged at its outer surface adapted to axially slide in at least one corresponding axial recess located in the inner surface of the second component. The important technical effect of this feature is the restoring force in the circumferential direction, i.e. the rotational forces which will cause the first component to move around the valve axis back into its original position where the resilient retention element is axially completely aligned with the corresponding axial recess of the second component. It should be noted that the sliding movement of the retention element within the axial recess in the axial direction is essential. In other words, the dimensions of the recess and the retention element must be such that the axial movement is ensured but that a rotation is still possible.

Preferably, the sealing component including the resilient portion and the resilient retention element are made of silicone rubber material. Silicone rubber is a well-known material for medical applications. It is relatively cheap and easy to manufacture, and comprises resilient characteristics among other characteristics which are beneficial in the medical field such as low toxicity, thermal stability, does not support microbiological growth, etc. It should be noted that other suitable materials may be used such as silicone-based deformable materials, thermoplastic elastomer material (TPE) or the like. Also, it is possible that the material of the resilient portion and/or the resilient retention element is not identical to the material of the rest of the sealing component. In other words, separate components could be arranged so as to form the sealing component having the resilient portion and the resilient retention element.

It is further preferred that the resilient portion comprises a hemispherical surface having one slit or at least two slits each extending from a central point on the hemispherical surface. The hemispherical or generally arcuate, dome-shaped surface is best suited for any type of cylinder-type valve device having a circular cross-section. Other shapes such as an ellipsoidal shape or any other surfaces of revolution are also envisioned. One slit through the central point of the hemisphere already provides sufficient area for fluid flow when a mechanical force is applied on the surface. At the same time, the restoring forces are high. A plurality of slits extending from this central point provide an even larger opening and thus a larger passageway for the fluid while the restoring forces are still high enough to ensure the self-closing capabilities of the valve device.

It must further be noted that a "slit" in the resilient portion in the context of the present invention relates to a thin, narrow cut which enables the cutting surfaces to contact each other in a sealing fashion. The properties of the resilient material such as silicone rubber are such that the restoring forces provide a sufficient fluid-tight sealing function. Further, the thickness of the material of the resilient portion need not be equal over its entire surface: it is possible that the side walls are substantially thicker than the hemispherical portion of the sealing component. In general, the resilient portion shall be configured to substantially retain the same initial shape upon removing any mechanical force from its surface so as to provide the necessary fluid tightness.

It is preferred that the first and/or second component comprises a medical connecting portion such as a male Luer lock entry, male Luer lock exit, female Luer lock entry, female Luer lock exit, a catheter exit, and the like. A large variety of connections can be applied to the distal ends of the first and second components providing an extensive flexibility. It is noted that the valve mechanism of the present invention may also be applied in other fields than medical connectors such as hydraulic or other connectors where the advantageous characteristics of the subject matter of the present invention can be beneficial.

It is further preferred that the sealing component comprises a flange portion connected to the first component in a press fit. Such a connection ensures that moving the first component with respect to the second component always includes the movement of the sealing component, particularly any axial and rotational movement. Therefore, the forces of a press fit must be such that the sealing component is continuously held tight on the first component. It is to be noted that such a press fit may also be achieved by additional supporting members such as a clamp or bracket or by any other suitable means. Optionally, a glue may be used to support the press fit of the sealing component on the first component. The flange portion of the sealing component may be configured to press fit into a corresponding groove on the first component.

Preferably, the latch comprises a grip portion extending through the recess beyond the outer surface of the first component wherein pressing the grip portion will release the engagement of the latch with the recess.

BRIEF DESCRIPTION OF THE DRAWINGS

The above object, features and advantages of the present invention will become apparent from a consideration of the following detailed description presented in connection with the accompanying drawings in which.

DETAILED DESCRIPTION OF PREFERRED EMBODIMENTS

Figure 1:
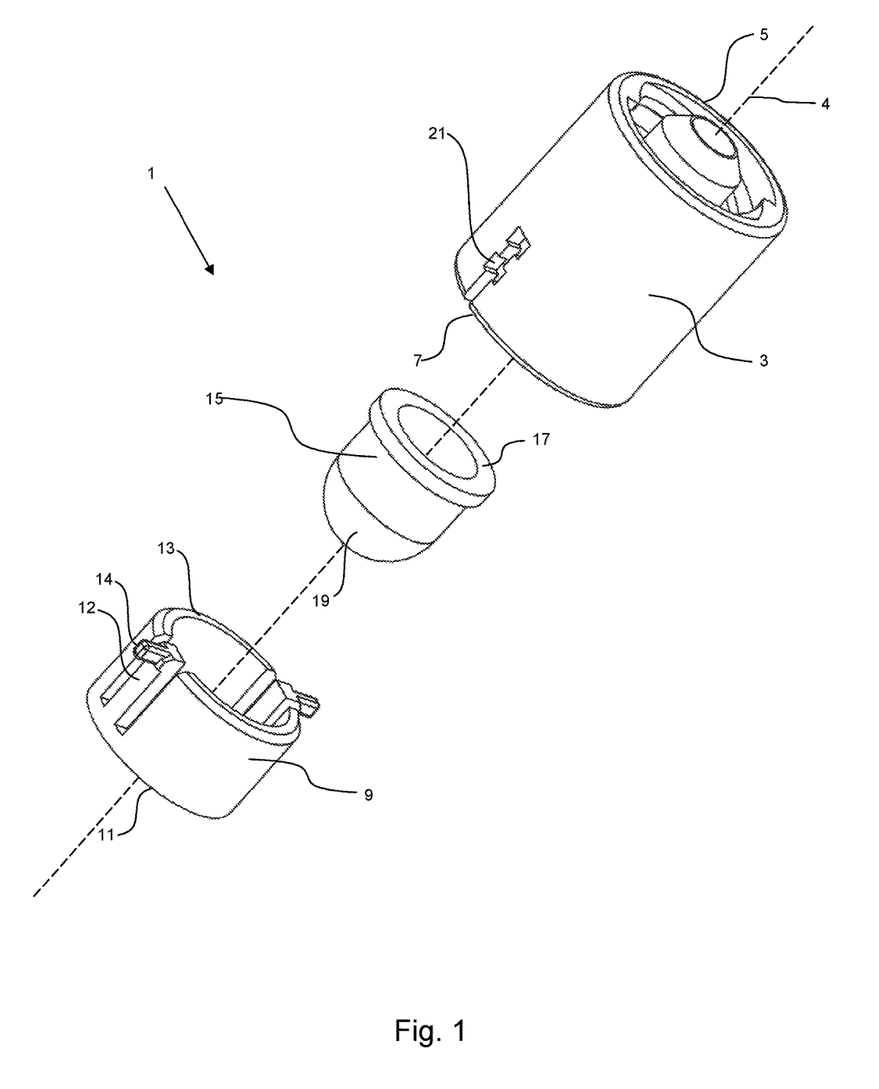
FIG. 1 shows an exploded perspective view of a first embodiment of the valve device according to the invention.

FIG. 1 shows an exploded perspective view of a first embodiment of the valve device. Valve device 1 includes a first component 3 embodied as a sleeve, a second component 9 and a sealing component 15 which in the operating configuration is arranged between the first component 3 and the second component 9, all along valve axis 4. First component 3 comprises a connector end 5 which in the illustrated embodiment is shaped as a standardized enteral male connector with a threaded portion and a central male portion. It should be noted that the connector end 5 of first component 3 can assume all kinds of connector portions which may have different configurations depending on the characteristic of the connector type. The sleeve-like first component 3 in this first embodiment comprises a substantially cylindrical shape having two openings or recesses 21 arranged on opposite sides near valve end 7.

Second component 9 is also embodied as a substantially cylindrically shaped sleeve adapted to fit within the inner diameter of first component 3. Second component 9 comprises a valve end 13, a connector end 11 and two latches 12 arranged on opposite sides of the outer surface of second component 9. The latches 12 extend substantially from the connector end 11 of the second component 9 parallel to the longitudinal axis of second component 9 and each comprise a grip protrusion 14 extending radially outward from the valve end 13.

Sealing component 15 which is in the operating position arranged between first component 3 and second component 9 comprises also a substantially cylindrical shape with a flange portion 17 at the end towards the first component 3, a substantially cylindrical middle portion and a resilient portion 19 located at the end which is near the second component 9. The flange portion 17 is adapted to be connected to first component 3 near valve end 7 inside the sleeve-like first component 3 in a press fit configuration. This means that when the sealing component 15 is connected to first component 3, a movement of the first component 3 will also cause sealing component 15 to move because both components are tightly fixed to each other.

The latches 12 with their grip protrusions 14 are adapted to be inserted into the recesses 21 on first component 3 when the valve device 1 according the invention is operable. In the following, the function of this first embodiment of the valve device will be explained in more detail with respect to FIGS. 2 to 5.

Figure 2:
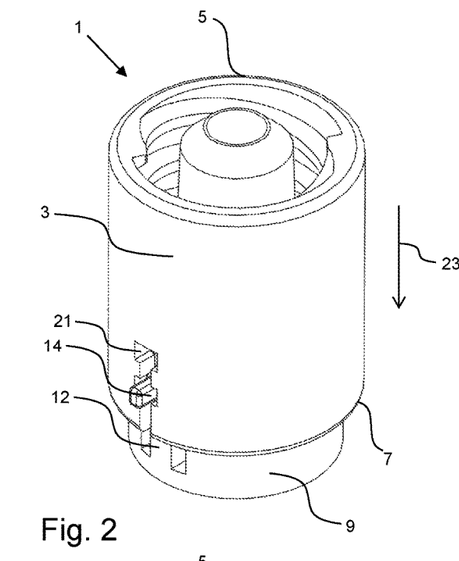
FIG. 2 shows a perspective view of the first embodiment of the valve device according to the invention in the closed configuration.

FIG. 2 shows a perspective view of the first embodiment of valve device 1 in the closed configuration. Second component 9 is connected to first component 3 with the sealing component 15 arranged in between (not shown). In the closed configuration depicted in FIG. 2 the latches 12 with the grip protrusion 14 are engaged with the lower portion of recess 21 in the outer surface of first component 3. It must be noted that the structure of the embodiment depicted in FIG. 2 comprises a short portion of second component 9 extending from the valve end 7 of first component 3. This portion may have other dimensions depending on the type of connection at connector end 11 of second component 9.

Figure 3:
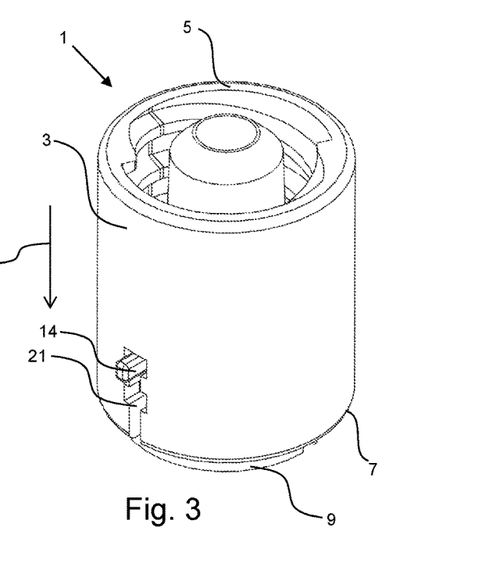
FIG. 3 shows a perspective view of the first embodiment of the valve device according to the invention in the open configuration.

FIG. 3 shows a perspective view of the first embodiment of valve device 1 in the open configuration meaning that first component 3 having sealing component 15 tightly connected in the inside thereof has been pressed onto second component 9 in the opening direction 23. As can be seen in FIG. 3 the latches 12 with their grip protrusions 14 are now engaged with the upper portion of the corresponding recesses 21 on first component 3.

Figure 4:
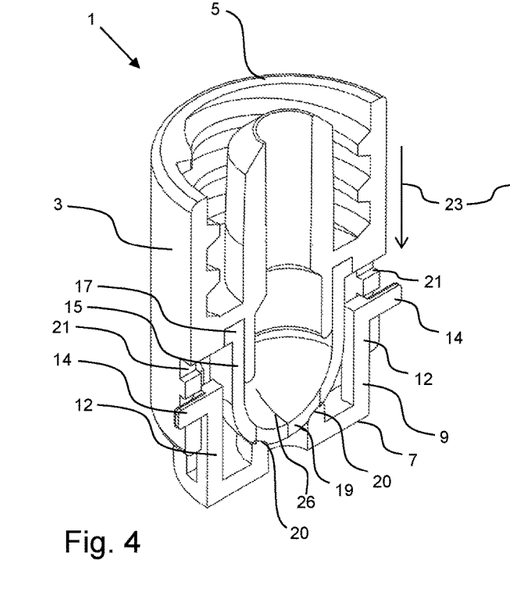
FIG. 4 shows a perspective cross-sectional view of the first embodiment of the valve device according to the invention in the closed configuration.
Figure 5:
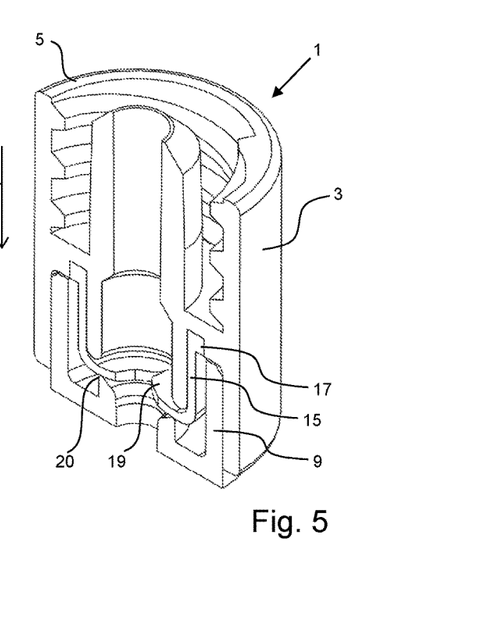
FIG. 5 shows a perspective cross-sectional view of the first embodiment of the valve device according to the invention in the open configuration.

FIG. 4 shows a perspective cross-section view of the first embodiment of the valve device in the closed configuration, which is a cross-sectional view in the plane defined by the longitudinal axis and the two recesses 21 depicted in FIG. 2. When looking at the latch 12 and the interaction with the outer surface of first component 3 the switching between the open and the closed configuration can be understood. In the closed configuration grip protrusion 14 engages with the lower portion of recess 21. By pressing onto grip protrusion 14 in a radial direction the latch 12 will be disconnected from the lower portion of recess 21 such that the stop function of this engagement is no longer present and enables a longitudinal movement along the valve axis 4 of the valve device 1 in the opening direction 23. Moving first component 3 and thus sealing component 15 in the opening direction 23 will lead to an engagement of latch 12 within the corresponding upper portion of recess 21 functioning as a stop. For this embodiment, recess 21 is configured to comprise two widened portions, an upper and a lower portion, which are adapted to engage with the top end of latch 12 in the closed and open position, respectively.

During the movement of first component 3 towards second component 9 in the opening direction indicated with arrow 23, the contact surface in the lower portion of second component 9 will come into contact with the outer surface of the resilient portion 19 of sealing component 15. Since the resilient portion 19 comprises four slits 26 at the very end of the resilient portion 19, pressing the resilient portion 19 will give away to the mechanical force exerted by the contact surface 20 which is a circular surface on second component 9, on the outer surface of the resilient portion 19 which can be seen in FIG. 5. The four opening portions of the resilient portion 19 will give way and through the elastic properties of the resilient portion 19, an opening will be created through which fluid can pass such that a passage way is created between first component 3 and second component 9. In the cross-sectional view of FIG. 5 this opening of the sealing component 15 can be clearly seen.

Figure 6:
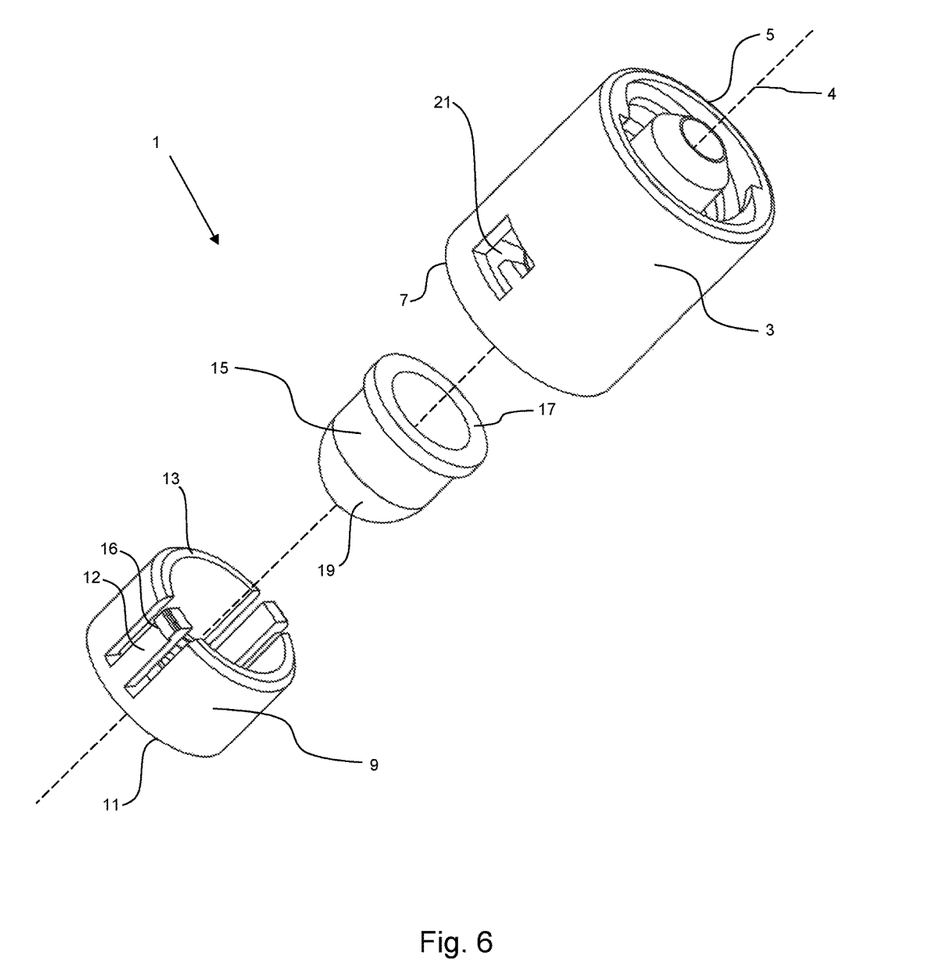
FIG. 6 shows an exploded perspective view of a second embodiment of the valve device according to the invention.

FIG. 6 shows an exploded perspective view of a second embodiment of the valve device. The configuration of the second embodiment is similar to the configuration of the first embodiment shown in FIG. 1. The difference lies in the locking mechanism which in the second embodiment comprises a different structure of recess 21 located on the outer surface of first component 3 and of latch 12 which extends from the connector end of second component 9. Similar to the first embodiment shown in FIGS. 1 to 5 there are two locking mechanisms located opposite to each other with respect to the longitudinal valve axis 4 of the valve device 1. It must be noted, however, that for all embodiments of the present invention there could be one or three or more locking mechanisms deployed on the outer surfaces of first component 3 and second component 9.

Recess 21 of first component 3 comprises a substantially rectangular configuration with a larger extension in the circumferential direction than in the axial direction parallel to the opening axis 23. Approximately in the middle of the longitudinal extension of recess 21 there is a locking arm 22 extending in a circumferential direction into recess 21 giving recess 21 a U-shape wherein the "U" is rotated by 90° with respect to the valve axis 4. In the embodiment shown as the second embodiment in FIGS. 6 to 10 the locking arm 22 extends from the right side wall in the outer surface of first component 3. The reason for this arrangement of locking arm 22 within recess 21 will become clear with respect to the detailed description of FIGS. 7 to 10 below.

The difference between the first and the second embodiment with respect to the latch 12 is that in the second embodiment of FIG. 6 the free end of latch 12 near the valve end 13 does not comprise a grip protrusion 14 as in the first embodiment. This means that in the second embodiment a manual pressing of the latch 12 radially in an inward direction from the outer surface of the valve device 1 is not necessary. This is due to the fact that in the second embodiment first component 3 is configured to be rotated around the longitudinal axis, and the dimensions of this rotation are determined by the dimensions of recess 21 along the circumferential direction of which latch 12 may be moved. The details of the rotational and longitudinal movement of first component 3 with respect to the second component 9 will now be described in detail with respect to FIGS. 7 to 10.

Before going into detail regarding the FIGS. 7 to 10 it must be noted that the locking mechanism according to the second embodiment is used in the optimal way when the connector port of first component 3 includes, for a superior performance of the valve, a threaded part similar to a Luer lock such that when another component is connected to first component 3 said other component must be turned clockwise in order to effect a proper connection. The clockwise connection movement of the other component with respect to the valve device 1 and also the disconnecting movement in the counterclockwise direction play an important role for the function of the locking mechanism according to the second embodiment. In combination with the turning or rotational movement in and against the opening direction 23 which is partly user initiated and partly an inherent movement due to the self-restoring properties of the sealing component 15, the movement in the circumferential direction, i. e. around the longitudinal valve axis 4 of the valve device 1, there are four main positions of the distal end of latch 12 within the area of recess 21.

Figure 7:
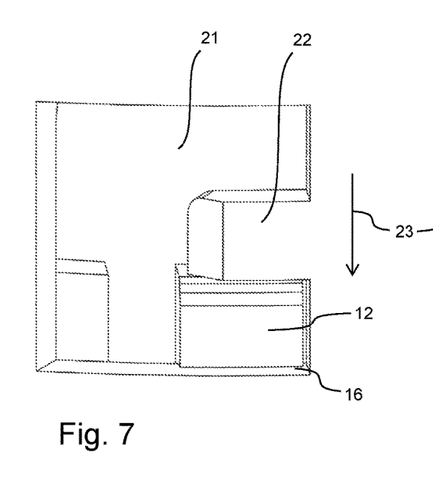
FIG. 7 shows a perspective view of a detail of the locking mechanism of the second embodiment in the closed configuration.

FIG. 7 shows a perspective view of the locking mechanism detail of the second embodiment in the closed configuration. As described with respect to FIGS. 2 to 5 the closed configuration is the configuration, where the first component 3 and the second component 9 are connected such that the circular contact surface 20 of second component 9 is slightly pressed against the resilient portion 19 of the sealing component 15, thus creating a sealing engagement of second component 9 with the resilient portion 19 closing the passageway through valve device 1. Upon pressing first component 3 onto second component 9 in the opening direction following arrow 23 along the valve axis 4 of valve device 1, the resilient portion 19 flexes or gives in to the mechanical force exerted by the inner part of second component 9 thus leading to an open passageway of valve device 1.

Considering this for the local interaction of latch 12 within recess 21 and locking arm 22, this means that in the closed position of FIG. 7 the first component 3 is in the position furthermost rotated in the clockwise direction within recess 21, and thus the right hand side edge of latch 12 abuts with the right side wall of recess 21 in the lower portion below locking arm 22. Latch 12 comprises at its end a protrusion 16 which engages with the lower edge of recess 21 such that first component 3 can not be easily moved in the longitudinal direction (opening/closing direction) with respect to second component 9. The engagement of the protrusion 16 with the lower wall of recess 21 prevents a disconnection of first component 3 from second component 9 against the opening direction indicated by arrow 23. An opening of valve device 1 by moving first component 3 towards second component 9 in order to close the valve is possible out of the position or configuration depicted in FIG. 7 although a self-opening of the valve is prevented by the protrusion 16 of latch 12 which would interact with the lower portion of locking arm 22.

Figure 8:
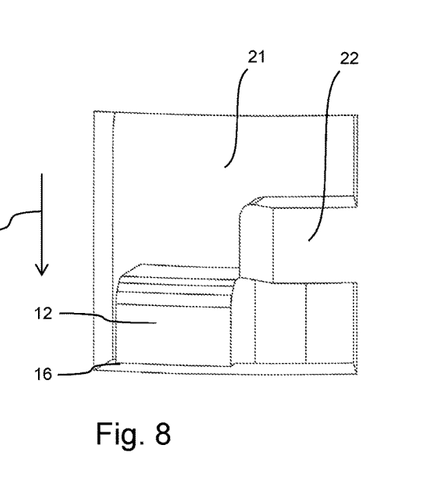
FIG. 8 also shows a perspective view of a detail of the locking mechanism of the second embodiment in the closed configuration.

FIG. 8 also shows a perspective view of the detailed locking mechanism of the second embodiment but in a configuration where the first component 3 has been rotated counterclockwise with respect to second component 9 by a predetermined angle which for example is determined to be 15°. Other angles are possible depending on the connector type such as between 5° and 40°. As can be understood, the width of the recess 21 determines the angle by which first component 3 may be rotated with respect to second component 9. In the second embodiment depicted in FIGS. 7 to 10 the width of latch 12 is a little larger than the width of locking arm 22, seen in the circumferential direction. In the configuration of FIG. 8 latch 12 has been moved to the lower left corner of the "window" of recess 21, and this configuration has been achieved by turning or rotating first component 9 counterclockwise with respect to second component 9. The protrusion 16 is still in engagement with the lower wall of recess 21 which still prevents the disconnection of first component 3 with second component 9. However, as there is no obstruction or barrier for latch 12 to be moved upwards in the window of recess 21, first component 3 may easily be moved towards second component 9 in order to open the valve.

Figure 9:
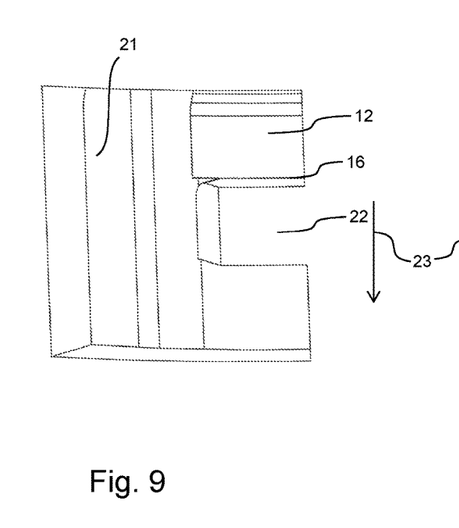
FIG. 9 shows a perspective view of a detail of the locking mechanism of the second embodiment in the open configuration.

FIG. 9 shows a perspective view of the detailed locking mechanism of the second embodiment in the open configuration, i. e. latch 12 is positioned in the upper right corner of "window" embodied by U-shaped recess 21. The protrusion 16 of latch 12 engages with the upper portion of locking arm 22 such that a movement along the longitudinal valve axis 4 against the opening direction indicated by arrow 23 is prevented by this engagement. The configuration depicted in FIG. 9 shows the rather stable, open configuration in the sense that first component 3 is still correctly connected with another component, and the disconnection of said other component with respect to the first component 3 necessarily implies a rotation of first component 3 with respect to second component 9 in the counterclockwise direction.

Figure 10:
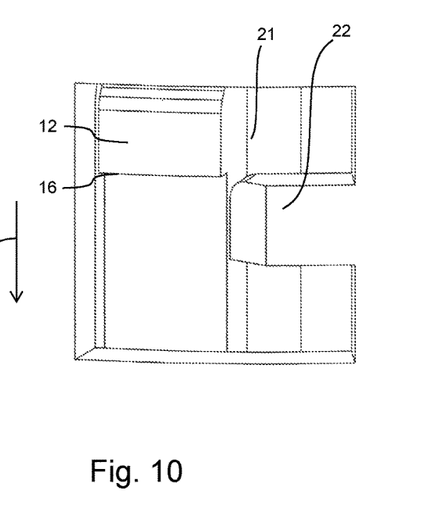
FIG. 10 also shows a perspective view of a detail of the locking mechanism of the second embodiment in the open configuration.

This counterclockwise rotation brings latch 12 into the configuration depicted in FIG. 10. In this position, latch 12 with protrusion 16 is no longer engaged with locking arm 22 such that the self-restoring forces of the resilient portion 19 of sealing component 15 will now force the movement of latch 12 towards the lower end or lower side wall of recess 21 to the position depicted in FIG. 8, which is the closed position.

In essence, when a user tries to disconnect the valve device 1 according to the second embodiment of the invention from the other component which is connected to first component 3 out of the open configuration shown in FIG. 9, the user will turn the first component 3 counterclockwise with respect to second component 9, arriving at the configuration in FIG. 10, and then the self-restoring forces of the resilient portion 19 of sealing component 15 will move second component 9 away from first component 3 such that the configuration depicted in FIG. 8 is achieved. Upon reconnecting another component to first component 3 by screwing e. g. a Luer lock into the port of first component 3, the clockwise movement of first component 3 will cause the valve device to achieve the configuration depicted in FIG. 7.

In this position a movement along the longitudinal valve axis 4 will open the valve because first component 3 and second component 9 are moved towards each other.

Figure 11:
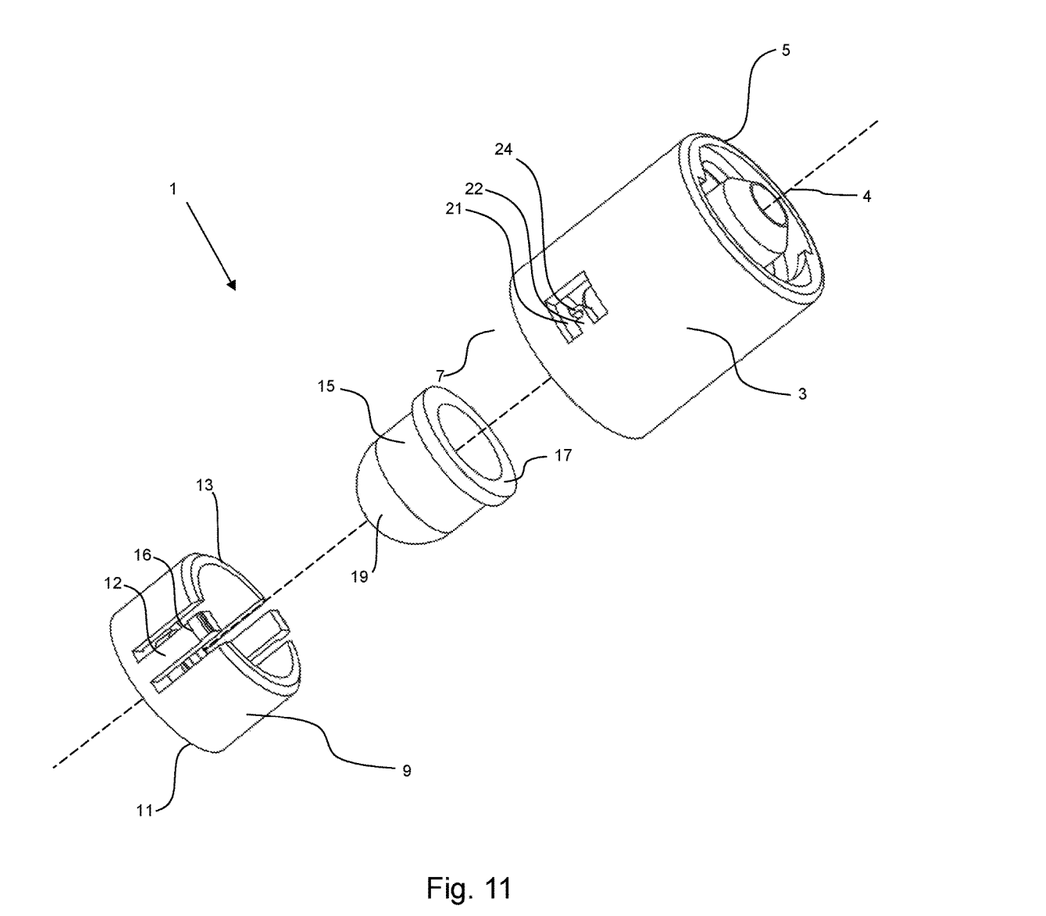
FIG. 11 shows an exploded perspective view of a third embodiment of the valve device according to the invention.

FIG. 11 shows an exploded perspective view of a third embodiment of the valve device. This embodiment is an improvement of the second embodiment of the present invention wherein the improvement lies only in the structure of the locking arm 22 located in the recess 21 of the locking mechanism located in a side wall of the sleeve-like first component 3. Since the components depicted in FIG. 11 are almost identical to the ones depicted in FIG. 6, the description of FIG. 6 is herewith referenced and repetitions or duplicates are avoided at this point. The only difference between the locking mechanisms of the second and third embodiment is the design of the locking arm 22. In the third embodiment the free end of the locking arm 22 comprises a spring element 24 which functions as a stop for the latch 12 in certain positions which will now be described in relation with FIGS. 12 to 15.

Figure 12:
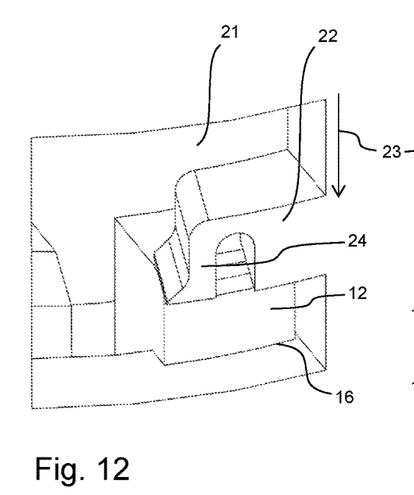
FIG. 12 shows a perspective view of a detail of the locking mechanism of the third embodiment in the closed configuration.

FIGS. 12 to 15 show perspective views of the locking mechanism details of the third embodiment in various configurations comparable to those shown in FIGS. 7 to 10 for the second embodiment. FIG. 12 shows the position of first component 3 with respect to second component 9 as described in relation with the second embodiment of FIG. 7, i. e. the latch 12 rests with the protrusion 16 against the lower wall of recess 21 in the lower right position of recess 21 such that the latch 12 is held by the lower side of locking arm 22 and the side wall of first component 3. This is the configuration which is achieved when the valve device is in the closed configuration and a further component is threadedly connected to the connector port of first component 3. There are two possibilities to move the valve device of the third embodiment out of this closed configuration depicted in FIG. 12. The first possibility is to rotate the first component 3 counterclockwise with respect to second component 9 in order to, e. g., threadedly disconnect the further component from first component 3.

Figure 13:
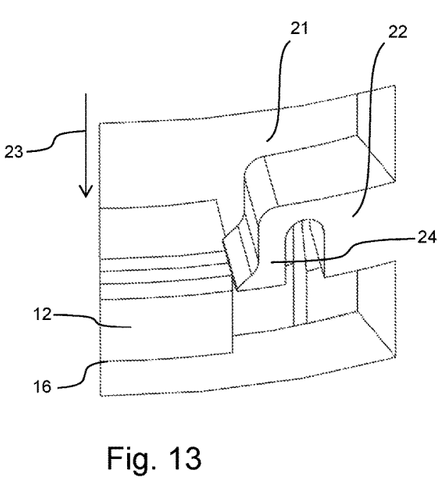
FIG. 13 also shows a perspective view of a detail of the locking mechanism of the third embodiment in the closed configuration.

The resulting configuration, which is still a closed configuration, is depicted in FIG. 13. The major difference to the position depicted in FIG. 8 of the second embodiment is, that the latch 12 is kept in this position by the stopping function of the spring element 24. As can be clearly seen in FIG. 13, the top side of latch 12 abuts the lower surface of spring element 24 which prevents latch 12 from moving upwards in the recess 21 which in turn would imply an (inadvertent) opening of the valve.

Figure 14:
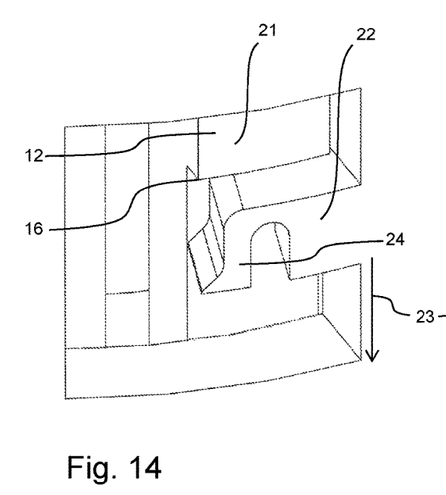
FIG. 14 shows a perspective view of a detail of the locking mechanism of the third embodiment in the open configuration.
Figure 15:
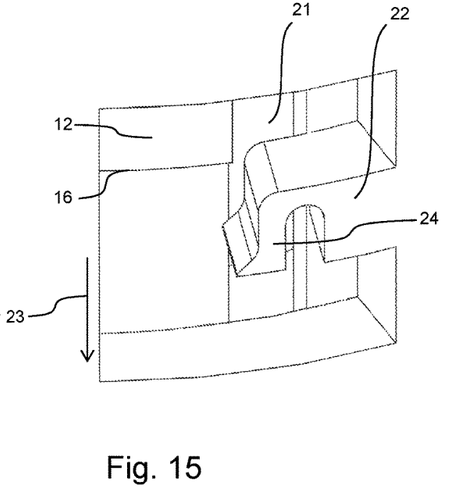
FIG. 15 also shows a perspective view of a detail of the locking mechanism of the third embodiment in the open configuration.

The other possibility of movement for latch 12 out of the closed configuration depicted in FIG. 12 is the general opening movement of the valve in the opening direction indicated by arrow 23 which means that the engagement of the latch 12 with the locking arm 22 is released and the first component 3 is moved towards second component 9 until finally the position depicted in FIG. 14 is reached. In this open configuration, the protrusion 16 of latch 12 is in engagement with the upper portion of locking arm 22 and generally latch 12 is located in the right half of recess 21. From this open position in FIG. 14, a rotational movement in the circumferential direction of the first component 3 with respect to the second component 9 leads to the configuration depicted in FIG. 15, i. e. the engagement of latch 12 with locking arm 22 is released and latch 12 is now in the upper left corner of recess 21 when looking at FIG. 15. This configuration is an unstable configuration in the sense that it is only temporary because the restoring forces of the resilient portion 19 of sealing component 15 will cause the automatic closing of the valve device 1 such that latch 12 will move along the longitudinal axis into the closed configuration shown in FIG. 13. Because of the elastic/resilient properties of spring element 24 the free end of spring element 24 is bent inwards, i. e. towards the fixed end of locking arm 22 such that the free end gives away to the vertical movement of latch 12. Thus, the third embodiment has the advantage of providing a safety stop for the valve device 1 after detaching a third component from first component 3 should it accidentally be pushed down into the open position. Thus, the situation is prevented that the connector port of first component 3 is open and at the same time the valve device is in the open position.

Figure 16:
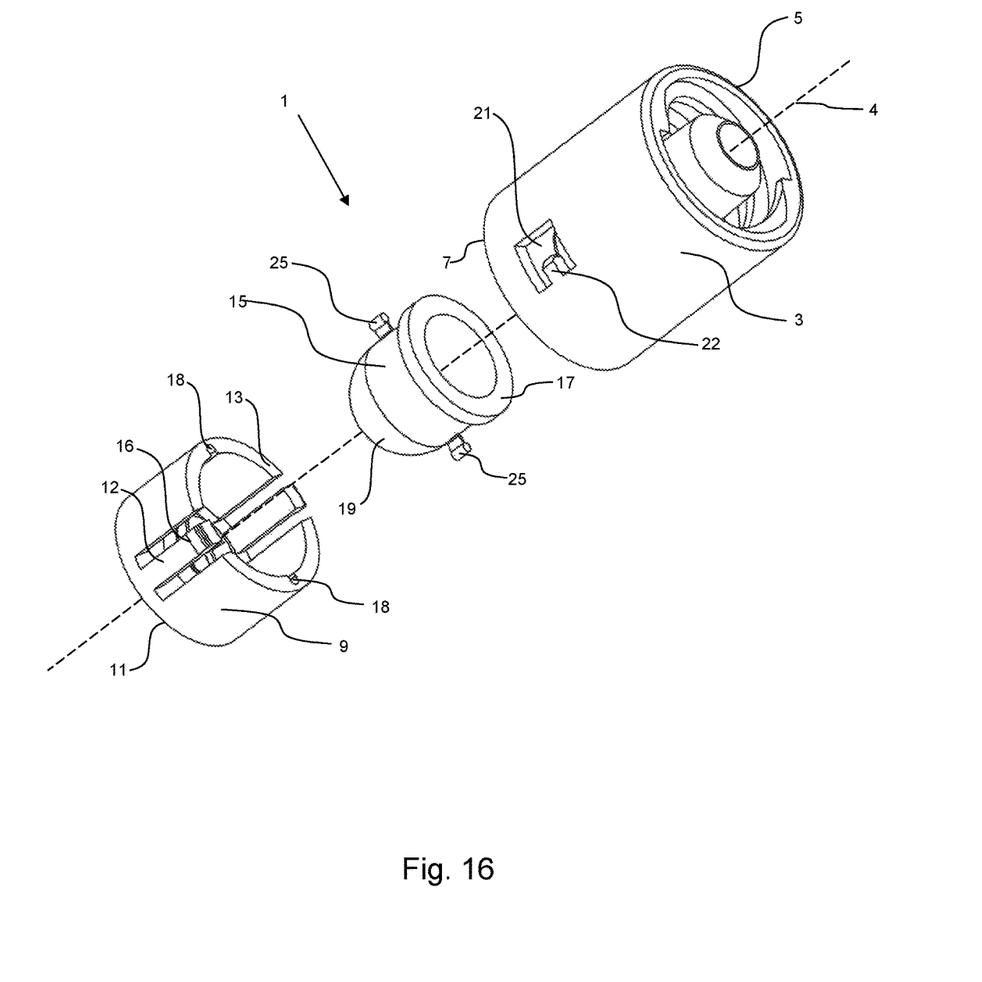
FIG. 16 shows an exploded perspective view of a fourth embodiment of the valve device according to the invention.

FIG. 16 shows an exploded perspective view of a fourth embodiment of the valve device. The configuration of the first component 3 of the fourth embodiment is identical to the one used in the second embodiment. Particularly, the locking arm 22 within the recess 21 does not comprise a spring element as in the third embodiment.

The difference between the fourth and the second or third embodiment lies therein that the sealing component 15 comprises two resilient retention elements 25 located in the cylindrical outer surface of the sealing component 15 which fit into corresponding axial recesses 18 arranged in the inner surface of the second component 9. In the shown embodiment the axial recesses run parallel to the longitudinal valve axis 4 of the valve device 1, and the function of these axial recesses 18 of which there are two on opposite sides of the second component 9 is to enable a rather smooth axial movement of the resilient retention elements 25 in the axial recesses 18 but to prevent a sliding out of the resilient retention elements 25 out of the axial recesses 18 when there is a rotational force around the valve axis 4 applied on the sealing component 15 which is firmly connected to first component 3.

In the two major configurations, the open and the closed configuration of the fourth embodiment, the position of first component 3 and second component 9 are such that they are essentially identical to the positions depicted in FIGS. 7 and 9 of the second embodiment. In other words, the locking mechanism of the fourth and the second embodiment with respect to the structure of the latch 12, protrusion 16 and locking arm 22 are identical. However, due to the retention mechanism which is embodied by the resilient retention element 25 and the axial recesses 18 in the second component 9, the procedure of operation of the fourth embodiment is different from the second embodiment. In particular, the configurations depicted in FIGS. 8 and 10 with regard to the second embodiment are only temporary configurations which will only be achieved when a user rotates the first component 3 counterclockwise with respect to the second component 9 out of the closed and open configuration.

It is the function of this retention mechanism that the positions of latch 12 on the right hand side of recess 21 are always assumed when a further component is disconnected from the connection port of the first component 3 or of the connection port of second component 9. The counterclockwise rotational movement to disconnect a threaded connector is countered by the retention force of the retention element 25 of sealing component 15.

It should be noted that the fourth embodiment with two retention elements 25 on sealing component 15 and the two corresponding recesses 18 in the second component 9 is only exemplary; there could be only one retention mechanism or more than two retention mechanisms. The number of such retention mechanisms will depend e.g. on the used material of the retention element 25 and the required retention force(s).

Figure 17:
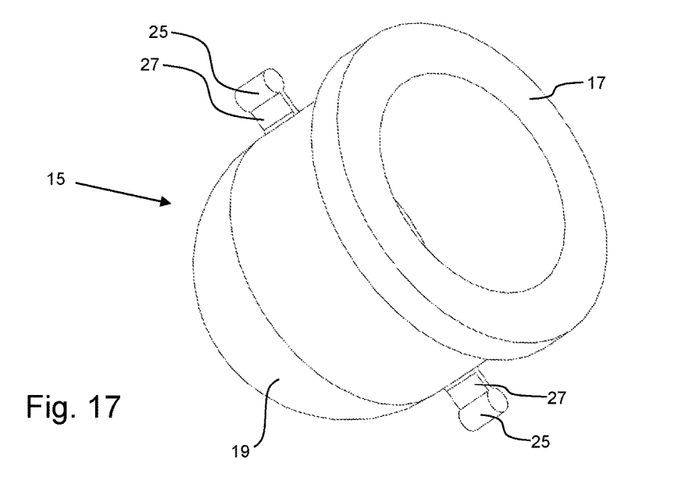
FIG. 17 shows a perspective view of the sealing component of the fourth embodiment of the valve device according to the invention.

FIG. 17 shows a perspective view of the sealing component 15 of the fourth embodiment of the valve device. In FIG. 17 it can be seen that the resilient retention elements 25 comprise an expansion portion 27 extending radially from the outer surface of the sealing component 15 which will expand upon rotation of the first component 3 with respect to the second component 9 and which functions as a spring due to the elastic characteristics of the material. When the first component 3 and thus the sealing component 15 are rotated with respect to the second component 9, the substantially cylinder-shaped portions of the retention elements 25 stay within the axial recesses 18 of second component 9 but the remainder of the sealing component 15 is rotated together with the first component 3. Due to the elastic characteristics of the expansion portion 27 there is a retention force in the circumferential direction working against the turning force of the user. Thus, the counterclockwise disconnecting movement of the first component 3 causes a corresponding retention force in the clockwise direction which will lead to the second component 9 rotating back into the configurations where the latch 12 is located at the right hand side of recess 21 in FIGS. 7 and 9, respectively.

The advantage of the locking mechanism including the retention mechanism between the sealing component 15 and the second component 9 is that rotating forces of the first component 3 will always be countered by the retention forces caused by the retention elements 25 of the sealing component 15 such that the user needs not bother about an inadvertent opening of the valve. It is thus ensured that upon connecting or disconnecting a third component to first component 3 on its connection port that in the closed position the valve device 1 will not open, and in the open position, the valve device will 1 automatically move into the closed position because of the self-restoring force of the resilient portion 19 of the sealing component 15 and due to the retention force of the retention elements 25 of sealing component 15.

Figures 18, 19:
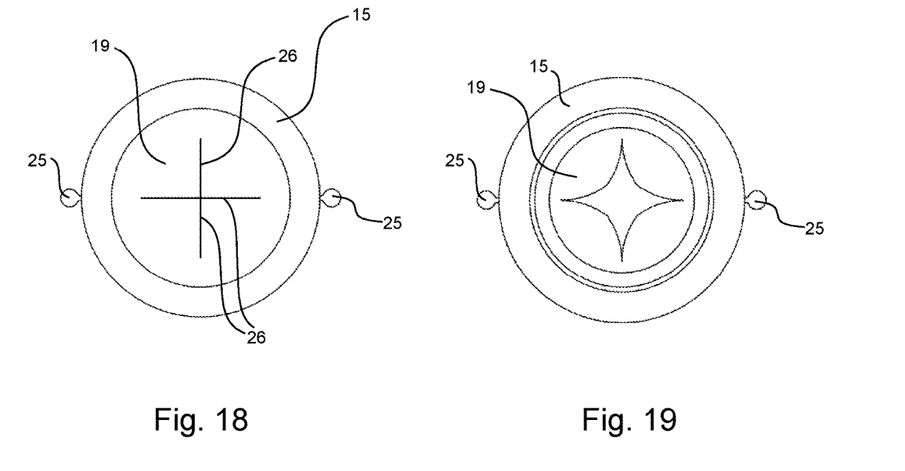
FIG. 18 shows a bottom view of the sealing component of the fourth embodiment of the valve device according to the invention in the closed configuration.
FIG. 19 shows a top view of the sealing component of the fourth embodiment of the valve device according to the invention in the open configuration.

FIG. 18 shows a bottom view of the sealing component 15 of the fourth embodiment of the valve device in the closed configuration. The slits 26 in this embodiment form a cross such that four slits of substantially equal length meet in one central point on the point of the hemispherical surface of the resilient portion 19 which is furthest in the opening direction. FIG. 19 shows a top view of the sealing component 15 of the fourth embodiment in the open configuration, in other words, FIG. 19 shows the view from the top in the open position, and FIG. 18 shows the view from the bottom in the closed position. It can be seen from FIG. 19 that the contacting surfaces of the slits 26 have given way to the mechanical force exerted by the contact surface(s) 20 of second component 9 such that an opening is created for the fluid to pass through the valve.

Figure 20:
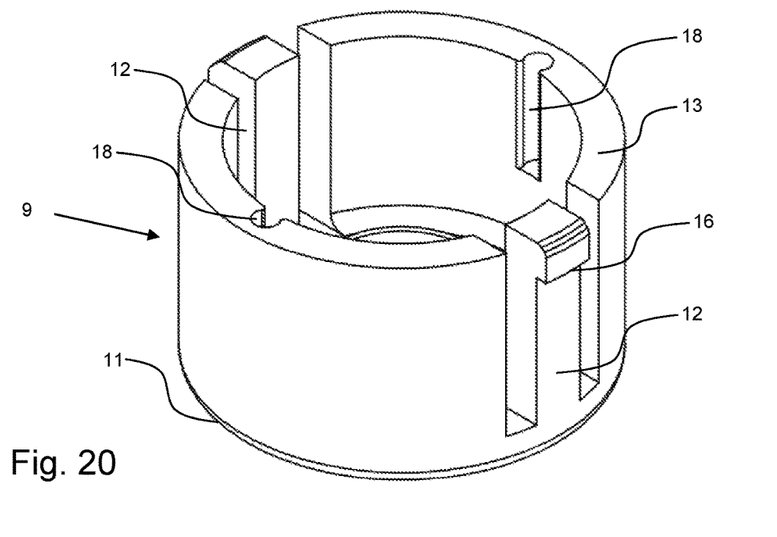
FIG. 20 shows a perspective view of the second component of the fourth embodiment of the valve device according to the invention.
Figure 21:
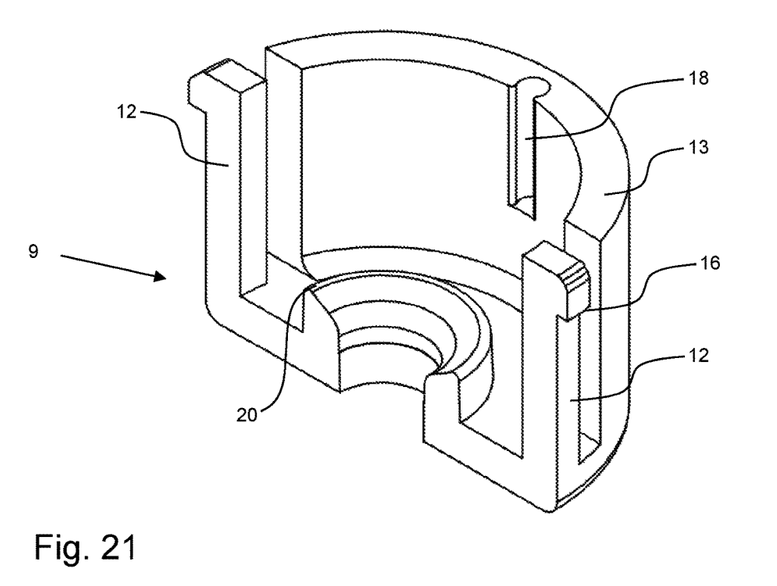
FIG. 21 shows a perspective cross-sectional view of the second component of the fourth embodiment of the valve device according to the invention.

FIGS. 20 and 21 show perspective and cross-sectional views of the second component 9 of the fourth embodiment of the valve device 1, respectively, with the axial recesses 18 clearly visible in the inner surface of second component 9. Extending from the connector end 11 of second component 9 is a substantially cylindrically shaped protrusion having a ring-like contact surface 20 which in the operating position(s) contacts the resilient portion 19 of sealing component 15. Other shapes of the contact surface 20 are possible which ensure a tight seal when the valve device is in the closed position and which ensure a sufficient size of the opening when the valve device is in the open position.

With the subject matter of the present invention a needle-free valve device has been provided which comprises a relatively simple structure, offers a wide variety of connection possibilities and is also self-sealing when disconnected from other ports.

The invention claimed is:

1. A needlefree valve device for controlling the flow of fluid in a pathway, the device having closed and open configurations and comprising:
   a first flow-through component;
   a second flow-through component;
   a sealing component having a resilient portion, the resilient portion comprising at least one slit;
   a locking member configured to selectively engage the first flow-through component with the second flow-through component in (a) the open configuration after the first flow-through component is displaced in an opening direction along a valve axis toward the second flow-through component for providing contact between a surface in a lower portion of the second flow-through component with the lower outer surface of the resilient portion of the sealing component; and (b) the closed configuration wherein the sealing component engages the second flow-through component to provide a seal after the first flow-through component is displaced against the opening direction away from the second flow-through component; and
   wherein the resilient portion is adapted to move, buckle or flex to enable fluid flow through the at least one slit upon application of a mechanical force of the second flow-through component on the resilient portion against the opening direction when assuming the open configuration, and wherein the resilient portion is adapted to return the valve device to the closed configuration when the mechanical force is no longer applied.

2. The needlefree valve device according to claim 1 wherein the first flow-through component, the second flow-through component and the sealing component are substantially axially aligned and the locking member is configured such that the first flow-through component is rotatable around the valve axis by a predetermined angle.

3. The needlefree valve device according to claim 1 wherein the locking member comprises a latch arranged on the second flow-through component adapted to engage with at least one corresponding recess in the first flow-through component.

4. The needlefree valve device according to claim 3 wherein the recess comprises a rectangular shape and a locking arm extending in a circumferential direction such that the latch of the second flow-through component is adapted to engage with the locking arm in the open and closed configurations.

5. The needlefree valve device according to claim 4 wherein the locking arm includes a spring element at its free end which functions as a stop for the latch in an axial direction.

6. The needlefree valve device according to claim 1 wherein the sealing component further comprises at least one resilient retention element arranged at its outer surface adapted to axially slide in at least one corresponding axial recess located on an inner surface of the second flow-through component.

7. The needlefree valve device according to claim 6 wherein the sealing component is made of silicone.

8. The needlefree valve device according to claim 1 wherein the resilient portion comprises a hemispherical surface having one slit or at least two slits each extending from a central point on the hemispherical surface.

9. The needlefree valve device according to claim 1 wherein the first or second flow-through components comprise a medical connecting portion selected from the group comprising a male Luer lock entry, male Luer lock exit, female Luer lock entry, female Luer lock exit, a catheter exit, and a tube mating port.

10. The needlefree valve device according to claim 1 wherein the sealing component comprises a flange portion connected to the first flow-through component in a press fit.

11. The needlefree valve device according claim 3 wherein the latch comprises a grip portion extending through the recess beyond the outer surface of the first flow-through component such that pressing the grip portion releases the engagement of the latch with the recess.

* * * * *